(12) United States Patent
Davis

(10) Patent No.: US 10,300,223 B2
(45) Date of Patent: May 28, 2019

(54) PLEURAL AIR LEAK TEST SYSTEM

(71) Applicant: Neomend, Inc., Irvine, CA (US)

(72) Inventor: Peter G. Davis, Dana Point, CA (US)

(73) Assignee: Neomend, Inc., Irvine, CA (US)

( * ) Notice: Subject to any disclaimer, the term of this patent is extended or adjusted under 35 U.S.C. 154(b) by 308 days.

(21) Appl. No.: 14/749,867

(22) Filed: Jun. 25, 2015

(65) Prior Publication Data

US 2015/0374936 A1 Dec. 31, 2015

Related U.S. Application Data

(60) Provisional application No. 62/016,898, filed on Jun. 25, 2014.

(51) Int. Cl.
| | |
|---|---|
| *A61B 5/00* | (2006.01) |
| *A61M 13/00* | (2006.01) |
| *A61M 16/08* | (2006.01) |
| *A61L 24/00* | (2006.01) |
| *A61L 24/10* | (2006.01) |
| *A61L 24/04* | (2006.01) |

(Continued)

(52) U.S. Cl.
CPC ............ *A61M 13/003* (2013.01); *A61B 5/08* (2013.01); *A61B 17/0057* (2013.01); *A61L 24/001* (2013.01); *A61L 24/0026* (2013.01); *A61L 24/043* (2013.01); *A61L 24/108* (2013.01); *A61M 16/0816* (2013.01); *A61B 2017/0065* (2013.01); *A61B 2017/00495* (2013.01); *A61M 11/00* (2013.01); *A61M 2202/0488* (2013.01); *A61M 2205/15* (2013.01); *A61M 2205/584* (2013.01)

(58) Field of Classification Search
CPC ............ A61B 17/0057; A61B 17/0065; A61B 17/00659; A61B 17/00663; A61B 5/08; A61M 15/0001; A61M 15/0065; A61M 15/009; A61L 24/001; A61L 24/0026; A61L 24/108; A61L 24/043
See application file for complete search history.

(56) References Cited

U.S. PATENT DOCUMENTS

| | | |
|---|---|---|
| 5,502,902 A | 4/1996 | Sussmann |
| 5,856,367 A | 1/1999 | Barrows et al. |

(Continued)

FOREIGN PATENT DOCUMENTS

WO WO 2013-123338 A1 8/2013

OTHER PUBLICATIONS

International Search Report and Written Opinion of the Korean Intellectual Property Office dated Sep. 25, 2015.

*Primary Examiner* — Max Hindenburg
(74) *Attorney, Agent, or Firm* — Wolf, Greenfield & Sacks, P.C.

(57) ABSTRACT

Disclosed are methods, apparatus, and systems useful for detecting leaks in pleural tissue. Also disclosed are methods of detecting and sealing such leaks. Indicator dye or stain is aerosolized and delivered to the lung via anesthetic equipment, oxygen tube, endoscope, or other suitable equipment, the dye is allowed to travel through the lung along the path or paths of least resistance emerging at the surface of the lung, staining the tissue indicative of a leak. Some embodiments include introducing one part of a two part sealant with the dye, and applying the second part of the sealant to the stain identified leak locations.

5 Claims, 2 Drawing Sheets

(51) Int. Cl.
*A61B 5/08* (2006.01)
*A61B 17/00* (2006.01)
*A61M 11/00* (2006.01)

(56) References Cited

U.S. PATENT DOCUMENTS

| | | |
|---|---|---|
| 6,371,975 B2 | 4/2002 | Cruise et al. |
| 6,458,095 B1 | 10/2002 | Wirt et al. |
| 6,458,147 B1 | 10/2002 | Cruise et al. |
| 6,569,113 B2 | 5/2003 | Wirt et al. |
| RE38,158 E | 6/2003 | Barrows et al. |
| 6,830,756 B2 | 12/2004 | Hnojewyj |
| 6,899,889 B1 | 5/2005 | Hnojewyj et al. |
| RE38,827 E | 10/2005 | Barrows et al. |
| 7,247,314 B2 | 7/2007 | Hnojewyj et al. |
| 7,318,933 B2 | 1/2008 | Hnojewyj |
| 7,766,891 B2 * | 8/2010 | McGurk .......... A61B 17/00491 604/506 |
| 7,766,938 B2 * | 8/2010 | McGurk .......... A61B 17/00491 530/350 |
| 8,034,367 B2 | 10/2011 | Hnojewyj |
| 8,409,605 B2 | 4/2013 | Hnojewyj et al. |
| 2005/0016542 A1 | 1/2005 | Wright |
| 2007/0251532 A1 | 11/2007 | Friedberg |
| 2010/0174270 A1 | 7/2010 | Charlez et al. |
| 2013/0245484 A1 | 9/2013 | Aljuri et al. |

\* cited by examiner

PLEURAL AIR LEAK TEST SYSTEM

CROSS-REFERENCE TO RELATED APPLICATIONS

This application claims priority to U.S. Provisional No. 62/016,898 entitled "PLEURAL AIR LEAK TEST SYSTEM" filed Jun. 25, 2014, which is hereby incorporated by reference in its entirety.

FIELD

Disclosed are methods, apparatus, and systems useful for detecting leaks in pleural tissue. Also disclosed are methods of detecting and sealing such leaks.

BACKGROUND

Detecting the location of a pleural air leak is a difficult task. Current methods include high resolution cat scans, MRIs, and bronchoscopy for direct visualization of proximal airway leaks and bronchopleural fistulas. These methods offer varying levels of reliability and satisfaction but are not consistently sensitive and accurate, and require the use of costly and time intensive apparatus, and may require that the patient be moved. One of the most definitive means to identify a pleural air leak is through the relatively crude technique of open thoracotomy, in which the chest cavity is opened and filled with saline solution and then, following positive pressure ventilation of the lung, the observation of bubble formation indicates air leakage and directionally points to the area of leakage.

Alternatively, this method may be performed by submerging portions of or the entire lung in saline and observing bubbles as an indicator for a leak.

Often in current surgical practice a surgeon does not perform a leak test at all, for many reasons, including but not limited to time demands, the physical manipulation needed to submerge the lung, the difficulty observing leaks on the posterior lung, and the difficulty in tracking an air bubble to its origin, difficulty in recognizing or marking the location for later treatment, etc.

Thus, among other things, it would be beneficial to provide a visual identifier for an air leak pathway or pathways.

SUMMARY OF INVENTION

Some embodiments provide a method of identifying and sealing an air leak in lung tissue in a patient in need thereof, the method comprising introducing a first composition comprising an indicator and a first component of a multi-part sealant into the lung via an aerosol or nebulizer, allowing the first composition to accumulate at one or more air leak, applying a second composition comprising a second component of a multi-part sealant externally to the lung at locations where the indicator has accumulated, and allowing the first component and the second component of the multi-part sealant to cure with one another to form a pleural sealant.

In some embodiments, the first composition is introduced to the patient in need thereof via the breathing apparatus.

Some embodiments provide a method of identifying and sealing an air leak in lung tissue in a patient in need thereof, the method comprising introducing an indicator compound into the lung via an aerosol or nebulizer, allowing the indicator compound to accumulate at one or more air leak, applying a suture or sealant at a location identified by accumulated indicator compound.

Some embodiments provide a pressurized canister for facilitating identification of pleural air leaks, the pressurized canister comprising a canister capable of holding a pressurized fluid; a pressurized fluid comprising one or more indicator compounds.

Some embodiments provide a pleural air leak detection kit, the kit comprising a pressurized canister for facilitating identification of pleural air leaks, the pressurized canister comprising a canister capable of holding a pressurized fluid, a pressurized fluid comprising one or more indicator compounds; and a dispenser apparatus for housing and actuating the pressurized canister, wherein the dispenser apparatus has a dispensing end capable of coupling to a breathing apparatus to permit flow of indicator compound into the lungs via the breathing apparatus.

In some embodiments the dispenser is adapted for coupling to a breathing tube.

These and other variants will be readily apparent to one of skill in the art in light of the present disclosure. The description herein is meant to be exemplary in nature.

DETAILED DESCRIPTION

Figure 1:
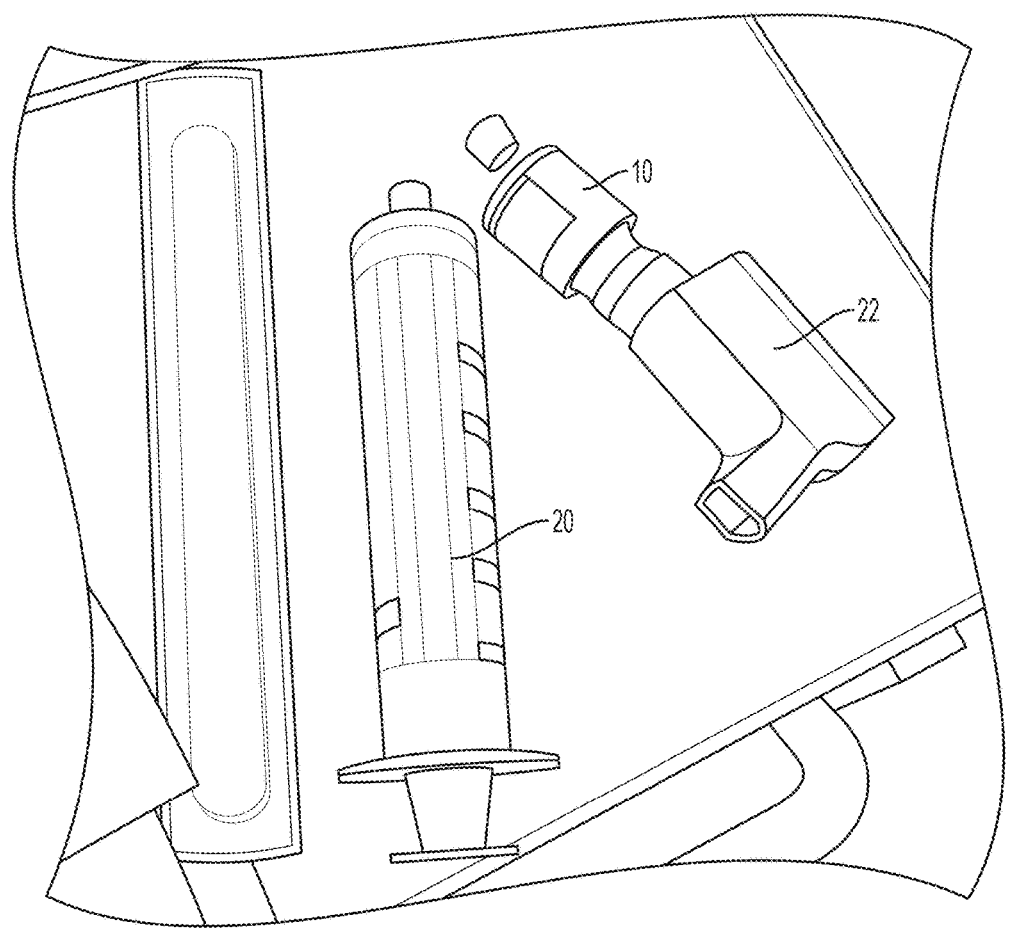
FIG. 1 depicts a two different introduction apparatus, a syringe and an aerosolizer both adapted to receive a pressurized canister containing the indicator.
Figure 2:
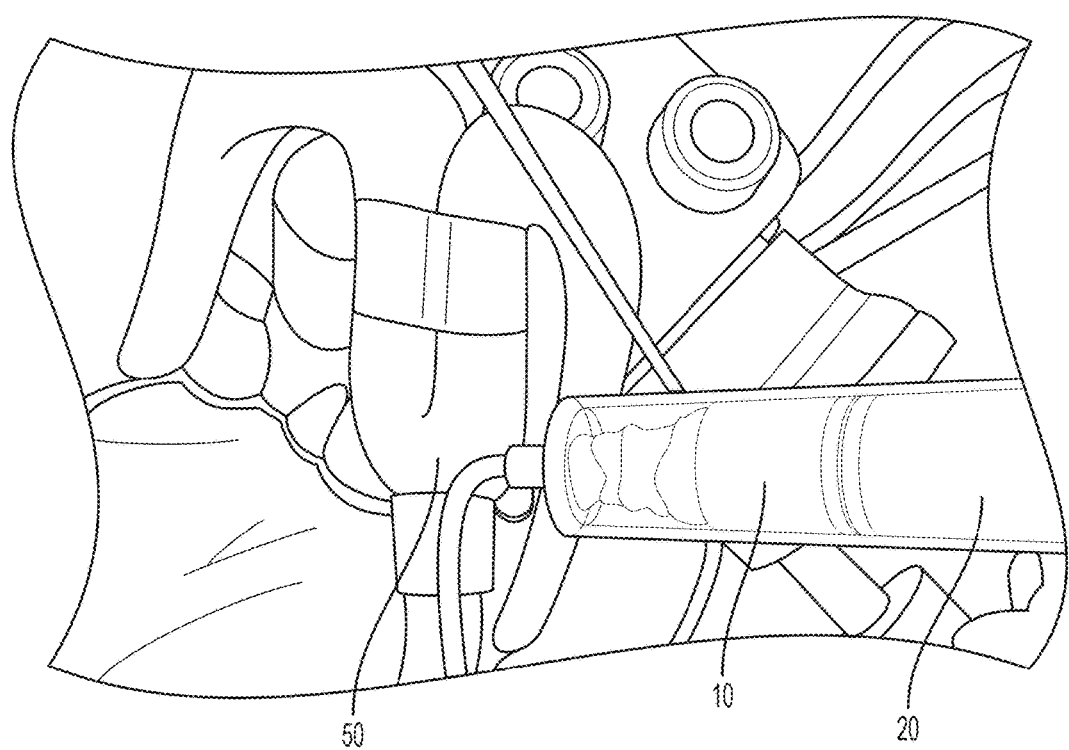
FIG. 2 depicts an exemplary system employing a syringe to introduce stain or dye into a tube leading to the lung.

Identifying and marking one or more pleural air leaks can be easily and conveniently accomplished by introducing an identifier, such as a stain or dye, into the lung. Introduction into the lung is accomplished by aerosolizing the stain or dye so it may travel through the airway(s). The identifier can be introduced to the lung via the normal airways, for example via the trachea, either or both of the main bronchi, or if desired at some other location. Upon introduction, the stain will travel most readily into the path or paths of least resistance, which will correspond to paths terminating in an air leak. The identifier will localize in or through the pathways ending in an air leak. On the exterior surface of the lung, the identifier will become visible, as it colors the exposed tissue at the leak site. Without the identifier, the exposed tissue is nearly impossible to distinguish from surrounding tissue. Once the identifier works its way through the pathway, it will be readily visible at the surface, exposing the leak for subsequent treatment, such as sealing.

The identifier may be any suitable medically acceptable dye, stain, or other colorant. Appropriate identifiers are easily visible against lung tissue, are biocompatible, and inert. In some embodiments, the identifier should not interfere with bleeding and should be substantially free of clumping to prevent blockage of the airways to be identified. The identifier may include a stain, such as but not limited to methylene blue or indocyanine green or FD&C blue or other FD&C approved colorants. The blue or green color of these identifiers is particularly visible against the red and pink color of the lung tissue permitting rapid identification by means of direct visualization of the location of a leak.

In some embodiments, the identifier has a viscosity and particle size sufficient to allow delivery as an aerosol or via nebulizer. In some embodiments, the identifier is a flowable aerosolizable particle capable of delivery to the lung parenchyma. In some embodiments, the identifier may be or may include a surfactant that has a starting low viscosity and small particle size such that it may be nebulized and delivered via anesthesia endoscope to the lung. In most instances, the identifier is most easily delivered via an endoscope into the lung. This may be accomplished with limited additional equipment, since the indicator may be introduced and aerosolized directly into an already existing anesthesia endoscope or, for example, oxygen supply tube.

The identifier could be a stain that is introduced into the lung via a breathing tube where the stain is aerosolized and can be transferred into the lung. The ideal stain will travel along the path of least resistance and focalize in or through an air leak pathway of the bronchioles of the lung. The stain is biocompatible and inert. The stain would not interfere with bleeding and can be a color easily seen on tissue. The ideal stain could be provided in an inhaler like unit (FIGS. 1, 2) that can be loaded into a section of the anesthesia equipment and expelled by pressure.

Once identified, the air leak can be addressed. In some embodiments, a pleural sealant, such as a hydrogel sealant such as those marketed by NEOMEND under the PROGEL brand name may be applied to the exterior of the lung, wherever indicator is present. In this manner, the air leak may be sealed. Any acceptable pleural air sealant may be used. Further examples of such hydrogel sealants can be found in US patents: U.S. Re38158; U.S. Re38827; U.S. Pat. No. 8,409,605; U.S. Pat. No. 5,502,902; U.S. Pat. No. 5,856,367; U.S. Pat. No. 6,371,975; U.S. Pat. No. 6,458,147; U.S. Pat. No. 6,899,889; U.S. Pat. No. 7,247,314; U.S. Pat. No. 6,830,756; U.S. Pat. No. 7,318,933; U.S. Pat. No. 8,034,367; U.S. Pat. No. 6,458,095; and U.S. Pat. No. 6,569,113, each of which is hereby incorporated in its entirety by reference.

In some embodiments, the indicator may be introduced into the lung at substantially the same time as a first component of a two part adhesive or sealant, such as those alluded to above. The indicator and first component are introduced as described above, via an aerosol or nebulizer, such that the indicator and first component are carried along the path or paths of least resistance to the air leak site or sites. In this manner, the first component of the adhesive or sealant is carried directly to the point of air leakage, along with the indicator. This, as above, is preferably done under pressure, which forces the indicator and first component to the air leak sites.

Because the indicator is visible on the surface of the lung at the air leak site or site, the leak sites are readily ascertainable, and a second component of the two component adhesive may be applied externally at those sites. This facilitates quick, consistent seal and avoids any possibility of inadvertent sealing within the lung. In some embodiments, the second component of the adhesive may also comprise a second indicator, such as a stain or dye. Upon application of the second component, the second indicator, which is different in color than the first and/or causes a color change, shows which leaks have been treated. For example, if the first component includes methylene blue as an indicator, the second component could include a yellow dye, such that the yellow either covers the blue or turns green when the two combine. In this manner, the surgeon is provided with immediate visual confirmation as to which air leaks have and have not been treated.

As described above, disclosed is a method of identifying and sealing a pleural air leak in a patient in need thereof. In accordance with some embodiments, the method comprises introducing an indicator and a first component of a multi-part sealant into the lung via an aerosol or nebulizer, allowing the indicator to accumulate at one or more air leak, applying a second component of a multi-part sealant externally to the lung at locations where the indicator has accumulated, and allowing the first component and the second component of the multi-part sealant to cure with one another to form a pleural sealant.

The multi-part sealant may be any suitable sealant. The multi-part sealant in some embodiments is readily formed from a two component mixture which includes a first part of a protein, preferably an albumin protein, such as human serum albumin or recombinant human albumin, in an aqueous buffer having a pH in the range of about 8.0-11.0 and a second part of a water-compatible or water-soluble bi-functional or multi-functional crosslinking agent or combinations thereof. When the two parts of the mixture are combined, the mixture is initially a liquid which cures in vivo on the surface of tissue in less than about one minute to give a strong, flexible, pliant substantive composition which bonds to the tissue and is absorbed in about four to sixty days. Particularly contemplated are two-part sealants which employ PEG and human albumin (natural or recombinant), such as those alluded to above.

To facilitate the introduction of the indicator, a pressurized canister containing the indicator, for example methylene blue, is provided. The canister is charged with a given amount of indicator at a given pressure sufficient to force the aerosolized indicator down a patient's breathing tube and into the airways. The breathing tube is managed by an anesthesiologist during the procedure which reduces the time the thoracic surgeon spends using saline to submerge the lung and looking for bubbles. Reduced surgical times are almost always beneficial to the patient. The clear presence of indicator on the surface of the lung at the point of air leakage provides a clear visual target for the surgeon, which in addition to saving time searching for leaks, allows for the opportunity to apply additional sutures or sealants with confidence. This should lead to better outcomes.

In some embodiments, the pressurized canister 10 containing the indicator may be a metered dose canister, similar to those used in an inhaler, which is capable of delivering a metered dose of the indicator. In other embodiments, the pressurized canister can be unmetered, with its contents released based upon user interaction. For example, the pressurized canister 10 can be placed in a delivery device such as a syringe 20, which is coupled to a patient's breathing tube 50, or other tube in communication with the lung or lungs, as seen in FIGS. 1 and 2. The user, for example the anesthesiologist, can control the flow of indicator into the patient's lung or lungs by depressing the syringe plunger, which in turn compresses the pressurized canister trigger mechanism to release its contents. The indicator is aerosolized as it leaves the pressurized canister and forced into the breathing tube as a result of the release of the pressure. In metered embodiments, a pre-set amount of indicator is released. In un-metered embodiments, the indicator flows freely from the pressurized canister until the user releases or pull back on the plunger to stop the flow. In either embodiment, the user may introduce 1 or more flows of indicator.

The pressurized canister may be charged with a composition which includes one or more indicator as described above, and one or more propellant. Any medically suitable propellant can be used. In some embodiments, the pressurized canister is sized for single use. By single use, it is meant a single surgical procedure. In some embodiments, the amount of indicator provided in a single canister is sufficient for testing the integrity of both lungs at least once. In some embodiments, a single canister may contain sufficient indicator for multiple tests during the same procedure.

Some embodiments provide a lung leak test kit including a pressurize canister housing an indicator, such as methylene blue or indocyanine green, a dispenser for housing the canister for fluid connection with a breathing tube, wherein the dispenser permits activation of the canister to release a metered amount of the indicator, or a free flow of the indicator.

What is claimed is:

1. A method of identifying and sealing an air leak in lung tissue in a patient in need thereof, the method comprising:
    introducing a first composition comprising an indicator and a first component of a multipart sealant into the lung via an aerosol or nebulizer,
    allowing the first composition to accumulate at one or more air leak,
    applying a second composition comprising a second component of a multi-part sealant externally to the lung at locations where the indicator has accumulated, and
    allowing the first component and the second component of the multi-part sealant to cure with one another to form a pleural sealant.

2. The method of claim 1, wherein the first composition is introduced to the patient in need thereof via a breathing apparatus.

3. A method of identifying and sealing an air leak in lung tissue in a patient in need thereof, the method comprising:
    introducing an indicator compound into the lung via an aerosol or nebulizer,
    allowing the indicator compound to accumulate at one or more air leak,
    applying externally to the lung a suture or sealant at a location identified by accumulated indicator compound.

4. The method of claim 1, wherein the indicator is methylene blue.

5. The method of claim 3, wherein the external application of the sealant also includes an application of an indicator.

* * * * *